US00PP30338P2

(12) United States Plant Patent
Tsukahara

(10) Patent No.: US PP30,338 P2
(45) Date of Patent: Apr. 2, 2019

(54) ***PETUNIA* PLANT NAMED 'SAKPET105'**

(50) Latin Name: *Petunia hybrida*
Varietal Denomination: SAKPET105

(71) Applicant: Sakata Seed Corporation, Yokohama (JP)

(72) Inventor: Jun Tsukahara, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 15/932,623

(22) Filed: Mar. 27, 2018

(51) Int. Cl.
*A01H 5/02* (2018.01)

(52) U.S. Cl.
USPC ..... Plt./356.13
CPC ..... *A01H 5/02* (2013.01)

(58) Field of Classification Search
USPC ..... Plt./356.13, 356.12
CPC ..... A01H 5/02
See application file for complete search history.

*Primary Examiner* — Kent L Bell
(74) *Attorney, Agent, or Firm* — Barbara Campbell; Cochran Freund & Young LLC

(57) ABSTRACT

A *Petunia* plant particularly distinguished by having burgundy and white star patterned flowers and a semi-trailing, and mounding habit, is disclosed.

1 Drawing Sheet

Genus and species: *Petunia hybrida.*
Variety denomination: 'SAKPET105'.

BACKGROUND OF THE NEW PLANT

The present invention comprises of a new and distinct cultivar of *Petunia*, botanically known as *Petunia hybrida*, and hereinafter referred to by the cultivar name 'SAKPET105.' 'SAKPET105' characterized by having a burgundy and white star pattern and mounding plant habit. 'SAKPET105' originated from a hybridization in Kakegawa, Japan in 2013. The female parent was a proprietary *Petunia* breeding line named '2ExTr-111a-V1' (unpatented) having a rose star pattern and a semi-mounding plant habit. The male parent was a proprietary *Petunia* breeding line named '2ExTr-111a-V2' (unpatented) having a rose star pattern and a semi-mounding plant habit.

In June 2013, '2ExTr-111a-V1' and '2ExTr-111a-V2' were crossed in Kakegawa, Japan and 300 seeds were obtained. In February 2014, the $F_1$ seed was sown in the greenhouse, cultivated and 140 plants were produced with flower colors of rose star pattern and rose with mounding, semi-mounding, and semi-creeping plant habits. In June 2014, five plant lines were selected within the $F_1$ plants that both had burgundy and white start pattern flowers and a mounding plant growth habit. A selection named 'L2015-PT032' was selected from these plant lines. From February to March 2015, 'L2015-PT032' was evaluated for day length neutral flowering response. From March to May 2015, 'L2015-PT032' was vegetatively propagated, cultivated and transplanted to the field for outdoor evaluation. From June to October 2015, the final selections were chosen and the mother stock was established. In January 2016, the breeder confirmed the line to be fixed and stable. The line was subsequently named 'SAKPET105' and its unique characteristics were found to reproduce true to type in successive generations of asexual propagation.

SUMMARY

The following are the most outstanding and distinguishing characteristics of this new variety when grown under normal horticultural practices in Salinas, Calif.

1. Burgundy and white star patterned flowers; and
2. A semi-trailing, and mounding habit.

DESCRIPTION OF THE PHOTOGRAPHS

This *Petunia* plant is illustrated by the accompanying photographs which show the plant's overall plant habit including form, foliage, and flowers. The photographs are of plants grown 3-months from transplant into 8-inch pots from rooted cuttings in Salinas, Calif. under greenhouse conditions. The colors shown are as true as can be reasonably obtained by conventional photographic procedures.

DESCRIPTION OF THE NEW VARIETY

Figure 1:
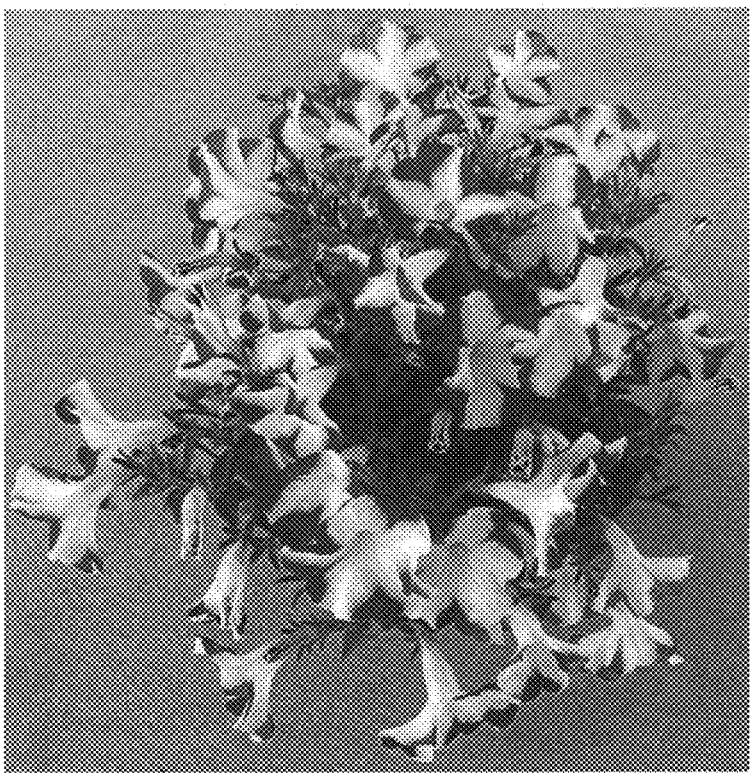
FIG. 1 shows the overall plant habit of the plant grown in a pot.
Figure 2:
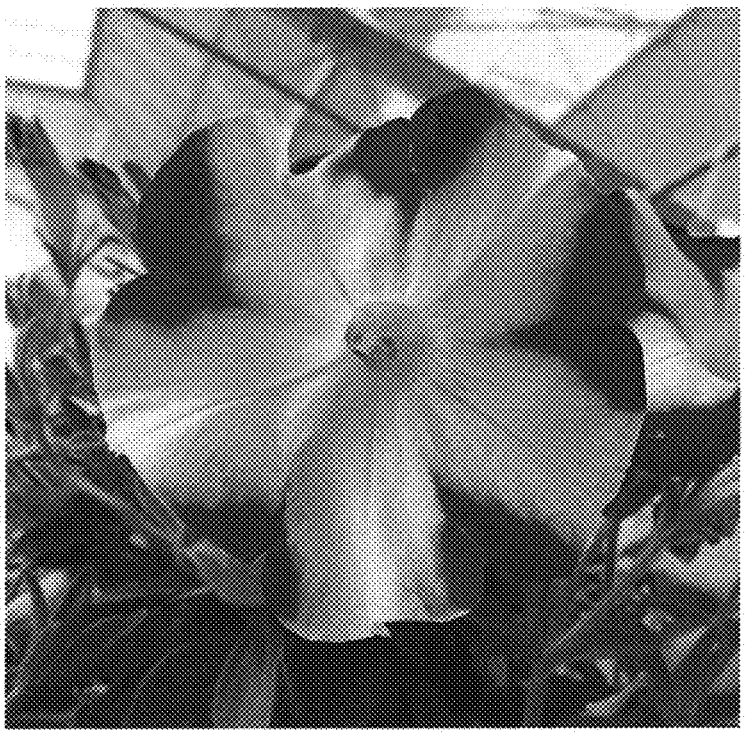
FIG. 2 shows a close-up of the mature flower of the plant.

The following traits and characteristics describe the new variety. Data obtained from plants grown 3-months from transplant into 8-inch pots from rooted cuttings in Salinas, Calif., under greenhouse conditions. Plants were pinched once during growth. Color references are to The Royal Horticultural Society of London color chart (R.H.S.), 4$^{th}$ edition (2001). Anatomic labels are from *The Cambridge Illustrated Glossary of Botanical Terms*, by M. Hickey and C. King, Cambridge University Press.

Classification:
*Family.*—Solanaceae.
*Botanical.—Petunia hybrida.*
*Common.—Petunia.*
*Designation.*—'SAKPET105'.

Growth: Environmental conditions for plant growth: The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Form*.—Semi-trailing.
*Habit*.—Mounding and semi-trailing.
*Height*.—About 19.0 cm from soil line to the top of the foliage.
*Spread*.—About 39.0 cm.
*Number of branches*.—6 main basal branches; many secondary and tertiary branches.
*Length of branches*.—13.5 cm to 19.0 cm.
*Diameter of branches*.—3.0 mm.
*Life cycle*.—Annual; tender perennial in warm climates.
*Time to produce a rooted cutting*.—About 4 weeks.
*Time to bloom from propagation*.—6 to 8 weeks.
*Flowering requirements* (*season*).—Will flower so long as temperature is above 13° C. and greater than 12 hours of daylight.
*Resistance and susceptibility to diseases and pests*.—No particular resistance or susceptibility observed.
*Temperature tolerances*.—No particular temperature tolerances observed.

Stems:

*Stem color*.—Closest to RHS 144B (Yellow-Green).
*Anthocyanin color*.—Absent.
*Stem pubescence*.—Heavy.
*Stem pubescence color*.—RHS N155A (White).
*Stem description*.—Pliable; circular shape in cross-section.
*Length*.—9.0 cm to 13.0 cm.
*Diameter*.—2.0 mm.
*Internode length*.—About 1.5 cm.

Leaves:

*Arrangement*.—Alternate.
*Shape*.—Ovate.
*Apex*.—Obtuse.
*Base*.—Attenuate.
*Attachment*.—Sessile.
*Margin*.—Entire.
*Surface appearance*.—Dull, waxy and sticky.
*Venation pattern*.—Pinnate.
*Venation color*.—Upper vein color: RHS 147C (Yellow-Green). Lower vein color: RHS 147C (Yellow-Green).
*Length*.—2.5 cm.
*Width*.—1.1 cm.
*Color*.—Upper surface: Closest to RHS 144A (Yellow-Green); more mature leaves are slightly darker on the upper surface, closest to RHS 137A (Green). Lower surface: Closest to RHS 146B (Yellow-Green).
*Variegation*.—Absent.
*Fragrance*.—Absent.
*Surface pubescence*.—Moderate.
*Surface pubescence color*.—RHS N155A (White).
*Petiole*.—Absent.

Flowers:

*Number of flowers in bloom*.—60.
*Number of flowers per node*.—1.
*Type*.—Soliltary.
*Fragrance*.—Absent.
*Flower depth*.—About 4.0 cm.
*Flower diameter*.—5.5 cm to 6.0 cm.
*Peduncle*.—Length: 2.1 cm. Diameter: 1.0 mm. Color: RHS 144B (Yellow-Green) with heavy pubescence; pubescence color is RHS N155A (White).

Bud:

*Bud surface*.—Dull, sticky, heavy pubescence; pubescence color is RHS N155A (White).
*Bud length*.—3.8 cm.
*Bud diameter*.—1.0 mm.
*Bud shape*.—Cylindrical.
*Bud color*.—Closest to RHS 145C (Yellow-Green) with RHS 145A (Yellow-Green) at the edges and closest to but darker than RHS 70A (Red-Purple) towards the tip with RHS N79A (Purple) at the very tip.

Corolla:

*Shape*.—Funnel-shaped with five fused petals.
*Diameter*.—5.5 cm to 6.0 cm.
*Depth*.—1.0 cm.
*Tube length*.—3.0 cm.
*Tube diameter*.—1.1 cm.
*Tube pubescence*.—Heavy.
*Tube pubescence color*.—RHS N155A (White).
*Color*.—Inner surface of tube: Closest to RHS 11A (Yellow) with RHS N155C (White), and RHS 144B (Yellow-Green) venation. Outer surface of tube: Closest to RHS 145C (Yellow-Green) with RHS 145C (Yellow-Green) venation.
*Petals*.—Pubescence: Glabrous. Length: 2.5 cm. Width: 2.9 cm. Shape: Obcordate. Apex: Dentate. Margin: Entire. Color: Upper surface: Closest to RHS N155B (White) in a five-point star pattern with points at mid-vein and outlined with RHS N74A (Red-Purple) with closest to but brighter and darker than RHS 72A (Red-Purple) surrounding the star pattern; RHS 144B (Yellow-Green) at the mid-vein. Lower surface: Closest to RHS 155C (White) but pure white in a five-point star pattern with points at mid-vein and RHS 72B (Red-Purple) surrounding star pattern. RHS 144B (Yellow-Green) mid-vein.

Sepals:

*Form*.—5, free.
*Attachment*.—Sessile.
*Apex*.—Obtuse.
*Base*.—Attenuate.
*Margin*.—Entire.
*Length*.—1.5 cm.
*Width*.—2.0 mm.
*Color*.—Upper surface: Closest to RHS 138A (Green). Lower surface: Closest to RHS 144A (Yellow-Green).

Reproductive organs:

*Stamens*.—Stamen form: Arranged adjacent to pistil. Stamen number: 5, free. Stamen length: 1.9 cm to 2.1 cm. Filament color: RHS 155C (White) but pure white. Anther color: RHS 155A (White). Pollen color: Closest to RHS 155A (White). Pollen description: Powdery; abundant.

*Pistil*.—Pistil number: 1. Pistil length: 2.0 cm. Stigma color: RHS 155A (White). Stigma length: 1.5 mm. Style color: RHS 145B (Yellow-Green). Style length: 1.8 cm. Ovary arrangement: Superior. Ovary surface color: RHS 144B (Yellow-Green).

*Seed production*.—Not observed.

COMPARISON WITH PARENTAL LINES AND KNOWN VARIETY

SAKPET105' is a new and distinct cultivar of *Petunia* owning to its burgundy and white star-patterned bi-colored flowers and mounding plant habit. 'SAKPET105' is most similar to the commercial *Petunia* variety COLORWORKS 'Violet Star', however, there are differences as listed in the table below:

TABLE 1

| Comparison with Similar Variety | | |
|---|---|---|
| Characteristic | 'SAKPET105' | COLORWORKS 'Violet Star' |
| Petal color, upper surface | Closest to RHS N155B (White) in a five-point star pattern with points at mid-vein and outlined with RHS N74A (Red-Purple) with closest to but brighter and darker than RHS 72A (Red-Purple) surrounding the star pattern; RHS 144B (Yellow-Green) at the mid-vein | Closest to RHS N78A (Purple) and RHS N155C (White) with RHS N79A (Purple) at mid-vein |

TABLE 1-continued

| Comparison with Similar Variety | | |
|---|---|---|
| Characteristic | 'SAKPET105' | COLORWORKS 'Violet Star' |
| Petal color, lower surface | Closest to RHS 155C (White) but pure white in a five-point star pattern with points at mid-vein and RHS 72B (Red-Purple) surrounding star pattern. RHS 144B (Yellow-Green) mid-vein | Closest to RHS 77A (Purple) and RHS N155C (White) |
| Flower diameter | 5.5 cm to 6.0 cm | 5.8 cm |
| Plant growth habit | Mounding | Mounding |

When 'SAKPET105' is compared to the parental lines, the following differences can be found below in Table 2.

TABLE 2

| Comparison with Parental Lines | | | |
|---|---|---|---|
| Characteristic | 'SAKPET105' | Female Parent '2ExTr-111a-V1' | Male Parent '2ExTr-111a-V2' |
| Flower color | Burgundy and white star pattern | Rose Star | Rose Star |
| Plant growth habit | Mounding | Semi-mounding | Semi-mounding |

I claim:

1. A new and distinct variety of *Petunia* plant named 'SAKPET105' as described and illustrated herein.

* * * * *